(12) United States Patent
Jo

(10) Patent No.: US 11,833,311 B2
(45) Date of Patent: Dec. 5, 2023

(54) MASSAGE CHAIR AND OPERATING METHOD THEREOF

(71) Applicant: LG ELECTRONICS INC., Seoul (KR)

(72) Inventor: Soonhaeng Jo, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 969 days.

(21) Appl. No.: 16/557,032

(22) Filed: Aug. 30, 2019

(65) Prior Publication Data
US 2019/0381271 A1 Dec. 19, 2019

(30) Foreign Application Priority Data
Aug. 9, 2019 (KR) .......................... 10-2019-0097482

(51) Int. Cl.
| | |
|---|---|
| *A61M 21/02* | (2006.01) |
| *G06N 3/08* | (2023.01) |
| *B60N 2/90* | (2018.01) |
| *G06F 3/04817* | (2022.01) |
| *G10L 15/22* | (2006.01) |

(Continued)

(52) U.S. Cl.
CPC ............... *A61M 21/02* (2013.01); *A61H 7/00* (2013.01); *B60N 2/976* (2018.02); *G06F 3/04817* (2013.01); *G06N 3/08* (2013.01); *G06V 40/161* (2022.01); *G08B 3/10* (2013.01); *G10L 15/08* (2013.01); *G10L 15/22* (2013.01); *A61H 2201/0149* (2013.01); *A61H 2201/5007* (2013.01); *A61H 2201/5043* (2013.01); *A61H 2201/5048* (2013.01); *A61M 2021/0022* (2013.01); *A61M 2021/0027* (2013.01); *A61M 2021/0083* (2013.01); *A61M 2205/3303* (2013.01); *A61M 2205/50* (2013.01); *A61M 2205/80* (2013.01); *G10L 2015/088* (2013.01); *G10L 2015/223* (2013.01)

(58) Field of Classification Search
CPC ............. A61M 21/00–02; B60N 2/976; A61H 2201/0149; G06N 3/02–049; A61B 5/4806–4818
See application file for complete search history.

(56) References Cited

U.S. PATENT DOCUMENTS

| | | | |
|---|---|---|---|
| 10,004,873 B1 * | 6/2018 | Hur ...................... | G05D 1/0274 |
| 2013/0194110 A1 * | 8/2013 | Kim ..................... | G06V 40/165 |
| | | | 340/905 |
| 2014/0009391 A1 * | 1/2014 | Van Lier ................. | G06T 7/246 |
| | | | 345/156 |

FOREIGN PATENT DOCUMENTS

JP 2012110528 A * 6/2012

OTHER PUBLICATIONS

English Translation of JP 2012/110528 A. (Year: 2012).*

* cited by examiner

*Primary Examiner* — Thaddeus B Cox
(74) *Attorney, Agent, or Firm* — Birch, Stewart, Kolasch & Birch, LLP

(57) ABSTRACT

An operating method of a massage chair comprising: driving the massage chair according to a massage mode; acquiring a user state; when he user state has a sleep mode, changing the massage mode to the sleep mode and driving the massage chair according to the changed sleep mode, and controlling an object related to the sleep mode to be adjusted; and driving the massage chair according to an optimal sleep mode by learning an artificial neural network (ANN) so as to acquire the optimal sleep mode corresponding to sleep habit pattern data in the sleep mode.

18 Claims, 9 Drawing Sheets

(51) Int. Cl.
*G10L 15/08* (2006.01)
*A61H 7/00* (2006.01)
*G08B 3/10* (2006.01)
*G06V 40/16* (2022.01)
*A61M 21/00* (2006.01)

MASSAGE CHAIR AND OPERATING METHOD THEREOF

CROSS REFERENCE TO RELATED APPLICATIONS

This non-provisional application claims the benefit under 35 U.S.C. § 119(a) to Patent Application No. 10-2019-0097482, filed in the Republic of Korea on Aug. 9, 2019, all of which is hereby expressly incorporated by reference into the present application.

BACKGROUND

An embodiment of the present invention relates to a massage chair and an operating method thereof, and in particular, to a massage chair having a customizing function according to a state of a user and an operating method of the massage chair.

Recently, apparatuses for maintaining or enhancing the health and physical strength of users or for fatigue recovery and stress reduction in the home, a gym, or the like, for example, a sporting apparatus such as a running machine or a massage apparatus have been developed and has been widely used in real life.

In particular, there has been a high demand for flexing the cramped muscle or overcoming fatigue and stress through massage, and thus a massage apparatus has attracted increasing attention. Massage is one of medical adjuvant therapies of helping blood circulation or fatigue recovery by sweeping, touching, pushing, pulling, tapping, or moving the body using hands or a specific apparatus. An apparatus for performing massage using a mechanical device is a massage apparatus, and a representative example of the massage apparatus is a massage chair for getting massage while a user comfortably sits thereon.

Recently, massage chairs have been developed to improve the user's convenience. Current massage chairs are not limited to simple massage functions, and function as enabling the user to get a massage conveniently, taking a rest and looking at various contents via wired and wireless communication, or going to sleep.

However, conventional massage chairs do not satisfy a function which the user desires, and also do not satisfy the user's convenience.

SUMMARY

Embodiments are to address the above-noted and other problems.

The other object of an embodiment is to provide a massage chair for satisfying various functions of a user, and an operation method of the massage chair.

Another object of an embodiment is to provide a massage chair which may increase a user's convenience, and an operating method of the massage chair.

According to an aspect of an embodiment to achieve the above-noted and other objects, an operating method of a massage chair includes the steps of: driving the massage chair according to a massage mode; acquiring a user state; when the user state has a sleep state, changing the massage mode to the sleep mode and driving the massage chair according to the changed sleep mode, and controlling an object related to the sleep mode to be adjusted; and driving the massage chair according to an optimal sleep mode by learning an artificial neural network (ANN) so as to acquire the optimal sleep mode corresponding to sleep habit pattern data in the sleep mode.

According to the other aspect of an embodiment, the massage chair includes: an ANN and a processor. The processor is configured to: drive the massage chair according to a massage mode; acquire a user state; when the user state has a sleep state, change the massage mode to a sleep mode and drive the massage chair according to the changed sleep mode, and control an object related to the sleep mode to be adjusted; and drive the massage chair according to an optimal sleep mode by learning the ANN so as to acquire the optimal sleep mode corresponding to sleep habit pattern data in the sleep mode.

The descriptions for effects of the massage chair and the operating method of the massage chair according to an embodiment will be described below.

According to at least one of embodiments, when the massage chair recognizes the user's sleep during operation in the massage mode, the massage mode may be changed to the sleep mode to operate the massage chair, and the massage chair may be allowed to operate in the optimal sleep mode by learning the sleep habit pattern data received during sleep, thus ensuring the sleep comfortability of the user and improving the user's convenience. In particular, according to an embodiment of the present invention, the sleep pattern data of the user is learned by the ANN, and thus the best sleep comfortability can be provided to the user not via an operating of the massage chair according to a fixed sleep mode but via an operation of the massage chair according to a consistently upgraded sleep mode.

According to at least one of embodiments, when the wake-up time comes, the user may be forced to wake up to help the user not to lose his/her schedule.

According to at least one of embodiments, the display unit may control its displacement to always face the user or be positioned around the user, by which the user can enjoy or conveniently use information displayed on the display unit. In addition, by moving the microphone around the user along with the display unit, the utterance of the user can be easily recognized to prevent malfunction caused by recognition faults.

According to at least one of embodiments, the user's convenience can be improved by providing an icon having a size suitable for the user.

According to at least one of the embodiments, when the user does not deviate from the massage chair after getting massage in the massage mode, the user's convenience can be improved by providing the user with a function that can be additionally performed.

Further scope of applicability of the present disclosure will become apparent from the detailed description given hereinafter. However, it should be understood that the detailed description and specific examples, while indicating preferred embodiments of the invention, are given by illustration only, since various changes and modifications within the spirit and scope of the invention will become apparent to those skilled in the art from this detailed description.

DETAILED DESCRIPTION OF THE EMBODIMENTS

<Artificial Intelligence (AI)>

Figure 1:
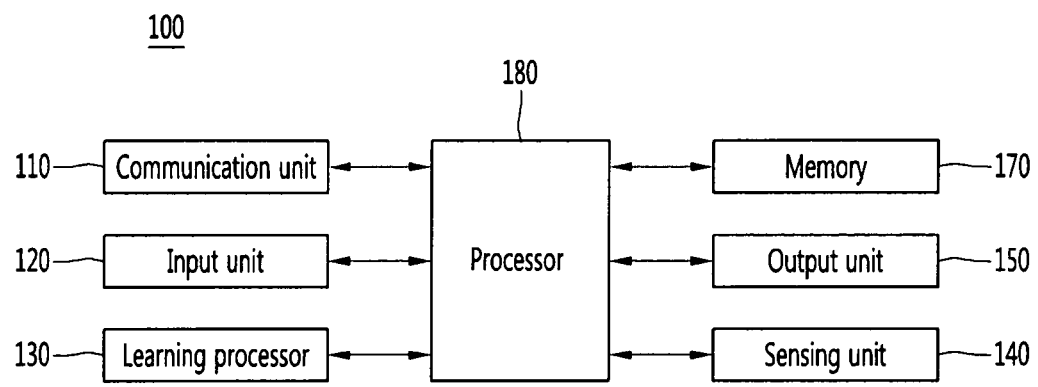
FIG. 1 illustrates an AI device 100 according to an embodiment of the present invention.

Artificial intelligence refers to the field of studying artificial intelligence or methodology for making artificial intelligence, and machine learning refers to the field of defining various issues dealt with in the field of artificial intelligence and studying methodology for solving the various issues. Machine learning is defined as an algorithm that enhances the performance of a certain task through a steady experience with the certain task.

An artificial neural network (ANN) is a model used in machine learning and may mean a whole model of problem-solving ability which is composed of artificial neurons (nodes) that form a network by synaptic connections. The artificial neural network can be defined by a connection pattern between neurons in different layers, a learning process for updating model parameters, and an activation function for generating an output value.

The artificial neural network may include an input layer, an output layer, and optionally one or more hidden layers. Each layer includes one or more neurons, and the artificial neural network may include a synapse that links neurons to neurons. In the artificial neural network, each neuron may output the function value of the activation function for input signals, weights, and deflections input through the synapse.

Model parameters refer to parameters determined through learning and include a weight value of synaptic connection and deflection of neurons. A hyperparameter means a parameter to be set in the machine learning algorithm before learning, and includes a learning rate, a repetition number, a mini batch size, and an initialization function.

The purpose of the learning of the artificial neural network may be to determine the model parameters that minimize a loss function. The loss function may be used as an index to determine optimal model parameters in the learning process of the artificial neural network.

Machine learning may be classified into supervised learning, unsupervised learning, and reinforcement learning according to a learning method.

The supervised learning may refer to a method of learning an artificial neural network in a state in which a label for learning data is given, and the label may mean the correct answer (or result value) that the artificial neural network must infer when the learning data is input to the artificial neural network. The unsupervised learning may refer to a method of learning an artificial neural network in a state in which a label for learning data is not given. The reinforcement learning may refer to a learning method in which an agent defined in a certain environment learns to select a behavior or a behavior sequence that maximizes cumulative compensation in each state.

Machine learning, which is implemented as a deep neural network (DNN) including a plurality of hidden layers among artificial neural networks, is also referred to as deep learning, and the deep running is part of machine running. In the following, machine learning is used to mean deep running.

<Robot>

A robot may refer to a machine that automatically processes or operates a given task by its own ability. In particular, a robot having a function of recognizing an environment and performing a self-determination operation may be referred to as an intelligent robot.

Robots may be classified into industrial robots, medical robots, home robots, military robots, and the like according to the use purpose or field.

The robot includes a driving unit may include an actuator or a motor and may perform various physical operations such as moving a robot joint. In addition, a movable robot may include a wheel, a brake, a propeller, and the like in a driving unit, and may travel on the ground through the driving unit or fly in the air.

<Self-Driving>

Self-driving refers to a technique of driving for oneself, and a self-driving vehicle refers to a vehicle that travels without an operation of a user or with a minimum operation of a user.

For example, the self-driving may include a technology for maintaining a lane while driving, a technology for automatically adjusting a speed, such as adaptive cruise control, a technique for automatically traveling along a predetermined route, and a technology for automatically setting and traveling a route when a destination is set.

The vehicle may include a vehicle having only an internal combustion engine, a hybrid vehicle having an internal combustion engine and an electric motor together, and an electric vehicle having only an electric motor, and may include not only an automobile but also a train, a motorcycle, and the like.

At this time, the self-driving vehicle may be regarded as a robot having a self-driving function.

<eXtended Reality (XR)>

Extended reality is collectively referred to as virtual reality (VR), augmented reality (AR), and mixed reality (MR). The VR technology provides a real-world object and background only as a CG image, the AR technology provides a virtual CG image on a real object image, and the MR technology is a computer graphic technology that mixes and combines virtual objects into the real world.

The MR technology is similar to the AR technology in that the real object and the virtual object are shown together.

However, in the AR technology, the virtual object is used in the form that complements the real object, whereas in the MR technology, the virtual object and the real object are used in an equal manner.

The XR technology may be applied to a head-mount display (HMD), a head-up display (HUD), a mobile phone, a tablet PC, a laptop, a desktop, a TV, a digital signage, and the like. A device to which the XR technology is applied may be referred to as an XR device.

FIG. 1 illustrates an AI device 100 according to an embodiment of the present invention.

The AI device 100 may be implemented by a stationary device or a mobile device, such as a TV, a projector, a mobile phone, a smartphone, a desktop computer, a notebook, a digital broadcasting terminal, a personal digital assistant (PDA), a portable multimedia player (PMP), a navigation device, a tablet PC, a wearable device, a set-top box (STB), a DMB receiver, a radio, a washing machine, a refrigerator, a desktop computer, a digital signage, a robot, a vehicle, and the like.

Referring to FIG. 1, the AI device 100 may include a communication unit 110, an input unit 120, a learning processor 130, a sensing unit 140, an output unit 150, a memory 170, and a processor 180.

The communication unit 110 may transmit and receive data to and from external devices such as other AI devices 100a to 100e and the AI server 200 by using wire/wireless communication technology. For example, the communication unit 110 may transmit and receive sensor information, a user input, a learning model, and a control signal to and from external devices.

The communication technology used by the communication unit 110 includes GSM (Global System for Mobile communication), CDMA (Code Division Multi Access), LTE (Long Term Evolution), 5G, WLAN (Wireless LAN), Wi-Fi (Wireless-Fidelity), Bluetooth™, RFID (Radio Frequency Identification), Infrared Data Association (IrDA), ZigBee, NFC (Near Field Communication), and the like.

The input unit 120 may acquire various kinds of data.

At this time, the input unit 120 may include a camera for inputting a video signal, a microphone for receiving an audio signal, and a user input unit for receiving information from a user. The camera or the microphone may be treated as a sensor, and the signal acquired from the camera or the microphone may be referred to as sensing data or sensor information.

The input unit 120 may acquire a learning data for model learning and an input data to be used when an output is acquired by using learning model. The input unit 120 may acquire raw input data. In this case, the processor 180 or the learning processor 130 may extract an input feature by preprocessing the input data.

The learning processor 130 may learn a model composed of an artificial neural network by using learning data. The learned artificial neural network may be referred to as a learning model. The learning model may be used to an infer result value for new input data rather than learning data, and the inferred value may be used as a basis for determination to perform a certain operation.

At this time, the learning processor 130 may perform AI processing together with the learning processor 240 of the AI server 200.

At this time, the learning processor 130 may include a memory integrated or implemented in the AI device 100. Alternatively, the learning processor 130 may be implemented by using the memory 170, an external memory directly connected to the AI device 100, or a memory held in an external device.

The sensing unit 140 may acquire at least one of internal information about the AI device 100, ambient environment information about the AI device 100, and user information by using various sensors.

Examples of the sensors included in the sensing unit 140 may include a proximity sensor, an illuminance sensor, an acceleration sensor, a magnetic sensor, a gyro sensor, an inertial sensor, an RGB sensor, an IR sensor, a fingerprint recognition sensor, an ultrasonic sensor, an optical sensor, a microphone, a lidar, and a radar.

The output unit 150 may generate an output related to a visual sense, an auditory sense, or a haptic sense.

At this time, the output unit 150 may include a display unit for outputting time information, a speaker for outputting auditory information, and a haptic module for outputting haptic information.

The memory 170 may store data that supports various functions of the AI device 100. For example, the memory 170 may store input data acquired by the input unit 120, learning data, a learning model, a learning history, and the like.

The processor 180 may determine at least one executable operation of the AI device 100 based on information determined or generated by using a data analysis algorithm or a machine learning algorithm. The processor 180 may control the components of the AI device 100 to execute the determined operation.

To this end, the processor 180 may request, search, receive, or utilize data of the learning processor 130 or the memory 170. The processor 180 may control the components of the AI device 100 to execute the predicted operation or the operation determined to be desirable among the at least one executable operation.

When the connection of an external device is required to perform the determined operation, the processor 180 may generate a control signal for controlling the external device and may transmit the generated control signal to the external device.

The processor 180 may acquire intention information for the user input and may determine the user's requirements based on the acquired intention information.

The processor 180 may acquire the intention information corresponding to the user input by using at least one of a speech to text (STT) engine for converting speech input into a text string or a natural language processing (NLP) engine for acquiring intention information of a natural language.

At least one of the STT engine or the NLP engine may be configured as an artificial neural network, at least part of which is learned according to the machine learning algorithm. At least one of the STT engine or the NLP engine may be learned by the learning processor 130, may be learned by the learning processor 240 of the AI server 200, or may be learned by their distributed processing.

The processor 180 may collect history information including the operation contents of the AI apparatus 100 or the user's feedback on the operation and may store the collected history information in the memory 170 or the learning processor 130 or transmit the collected history information to the external device such as the AI server 200. The collected history information may be used to update the learning model.

The processor 180 may control at least part of the components of AI device 100 so as to drive an application program stored in memory 170. Furthermore, the processor 180 may operate two or more of the components included in the AI device 100 in combination so as to drive the application program.

Figure 2:
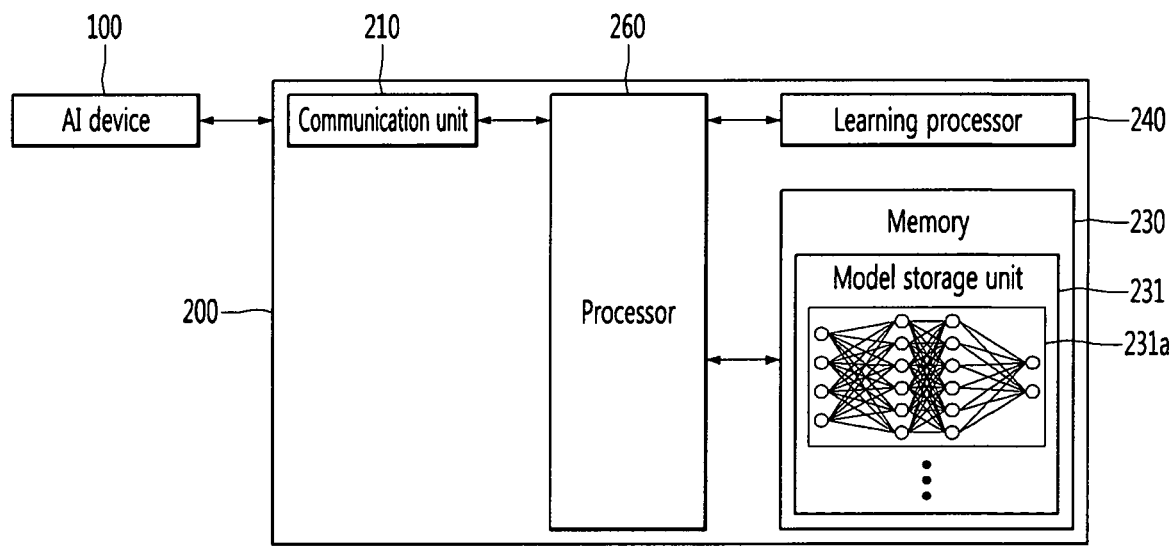
FIG. 2 illustrates an AI server 200 according to an embodiment of the present invention.

FIG. 2 illustrates an AI server 200 according to an embodiment of the present invention.

Referring to FIG. 2, the AI server 200 may refer to a device that learns an artificial neural network by using a machine learning algorithm or uses a learned artificial neural network. The AI server 200 may include a plurality of servers to perform distributed processing, or may be defined as a 5G network. At this time, the AI server 200 may be included as a partial configuration of the AI device 100, and may perform at least part of the AI processing together.

The AI server 200 may include a communication unit 210, a memory 230, a learning processor 240, a processor 260, and the like.

The communication unit 210 can transmit and receive data to and from an external device such as the AI device 100.

The memory 230 may include a model storage unit 231. The model storage unit 231 may store a learning or learned model (or an artificial neural network 231a) through the learning processor 240.

The learning processor 240 may learn the artificial neural network 231a by using the learning data. The learning model may be used in a state of being mounted on the AI server 200 of the artificial neural network, or may be used in a state of being mounted on an external device such as the AI device 100.

The learning model may be implemented in hardware, software, or a combination of hardware and software. If all or part of the learning models are implemented in software, one or more instructions that constitute the learning model may be stored in memory 230.

The processor 260 may infer the result value for new input data by using the learning model and may generate a response or a control command based on the inferred result value.

Figure 3:
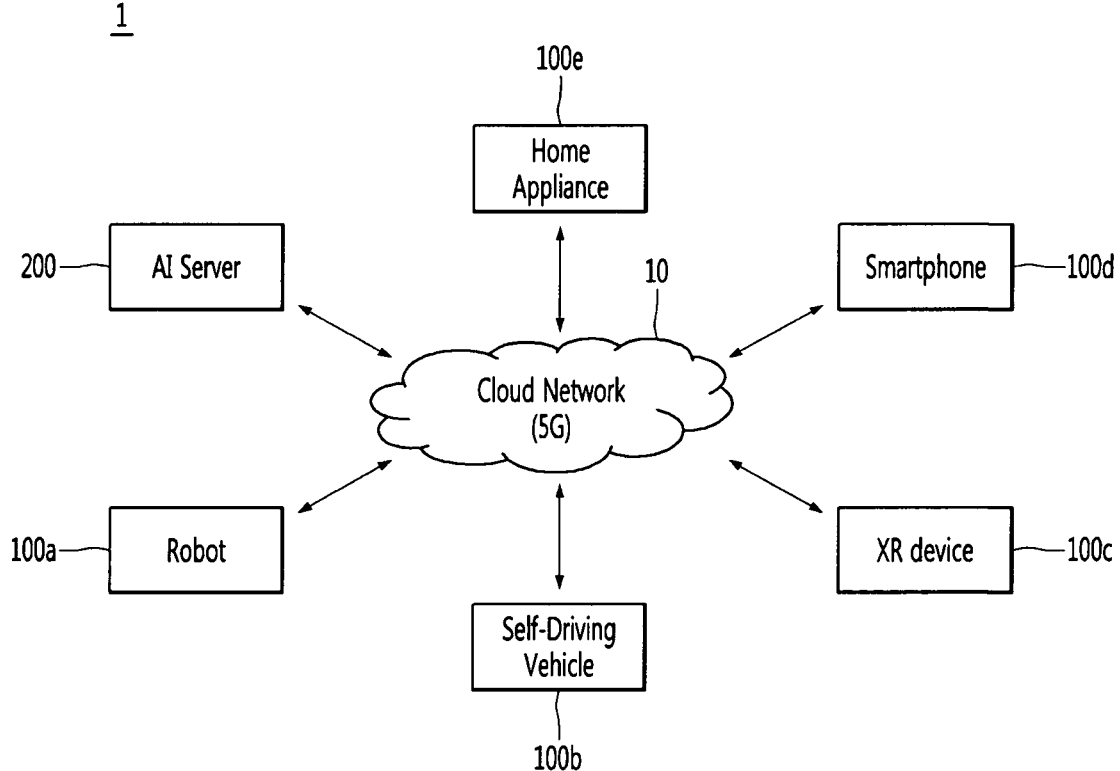
FIG. 3 illustrates an AI system 1 according to an embodiment of the present invention.

FIG. 3 illustrates an AI system 1 according to an embodiment of the present invention.

Referring to FIG. 3, in the AI system 1, at least one of an AI server 200, a robot 100a, a self-driving vehicle 100b, an XR device 100c, a smartphone 100d, or a home appliance 100e is connected to a cloud network 10. The robot 100a, the self-driving vehicle 100b, the XR device 100c, the smartphone 100d, or the home appliance 100e, to which the AI technology is applied, may be referred to as AI devices 100a to 100e.

The cloud network 10 may refer to a network that forms part of a cloud computing infrastructure or exists in a cloud computing infrastructure. The cloud network 10 may be configured by using a 3G network, a 4G or LTE network, or a 5G network.

That is, the devices 100a to 100e and 200 configuring the AI system 1 may be connected to each other through the cloud network 10. In particular, each of the devices 100a to 100e and 200 may communicate with each other through a base station, but may directly communicate with each other without using a base station.

The AI server 200 may include a server that performs AI processing and a server that performs operations on big data.

The AI server 200 may be connected to at least one of the AI devices constituting the AI system 1, that is, the robot 100a, the self-driving vehicle 100b, the XR device 100c, the smartphone 100d, or the home appliance 100e through the cloud network 10, and may assist at least part of AI processing of the connected AI devices 100a to 100e.

At this time, the AI server 200 may learn the artificial neural network according to the machine learning algorithm instead of the AI devices 100a to 100e, and may directly store the learning model or transmit the learning model to the AI devices 100a to 100e.

At this time, the AI server 200 may receive input data from the AI devices 100a to 100e, may infer the result value for the received input data by using the learning model, may generate a response or a control command based on the inferred result value, and may transmit the response or the control command to the AI devices 100a to 100e.

Alternatively, the AI devices 100a to 100e may infer the result value for the input data by directly using the learning model, and may generate the response or the control command based on the inference result.

Hereinafter, various embodiments of the AI devices 100a to 100e to which the above-described technology is applied will be described. The AI devices 100a to 100e illustrated in FIG. 3 may be regarded as a specific embodiment of the AI device 100 illustrated in FIG. 1.

<AI+Robot>

The robot 100a, to which the AI technology is applied, may be implemented as a guide robot, a carrying robot, a cleaning robot, a wearable robot, an entertainment robot, a pet robot, an unmanned flying robot, or the like.

The robot 100a may include a robot control module for controlling the operation, and the robot control module may refer to a software module or a chip implementing the software module by hardware.

The robot 100a may acquire state information about the robot 100a by using sensor information acquired from various kinds of sensors, may detect (recognize) surrounding environment and objects, may generate map data, may determine the route and the travel plan, may determine the response to user interaction, or may determine the operation.

The robot 100a may use the sensor information acquired from at least one sensor among the lidar, the radar, and the camera so as to determine the travel route and the travel plan.

The robot 100a may perform the above-described operations by using the learning model composed of at least one artificial neural network. For example, the robot 100a may recognize the surrounding environment and the objects by using the learning model, and may determine the operation by using the recognized surrounding information or object information. The learning model may be learned directly from the robot 100a or may be learned from an external device such as the AI server 200.

At this time, the robot 100a may perform the operation by generating the result by directly using the learning model, but the sensor information may be transmitted to the external device such as the AI server 200 and the generated result may be received to perform the operation.

The robot 100a may use at least one of the map data, the object information detected from the sensor information, or the object information acquired from the external apparatus to determine the travel route and the travel plan, and may control the driving unit such that the robot 100a travels along the determined travel route and travel plan.

The map data may include object identification information about various objects arranged in the space in which the robot 100a moves. For example, the map data may include object identification information about fixed objects such as walls and doors and movable objects such as pollen and desks. The object identification information may include a name, a type, a distance, and a position.

In addition, the robot 100a may perform the operation or travel by controlling the driving unit based on the control/interaction of the user. At this time, the robot 100a may acquire the intention information of the interaction due to the user's operation or speech utterance, and may determine the response based on the acquired intention information, and may perform the operation.

<AI+Self-Driving>

The self-driving vehicle 100b, to which the AI technology is applied, may be implemented as a mobile robot, a vehicle, an unmanned flying vehicle, or the like.

The self-driving vehicle 100b may include a self-driving control module for controlling a self-driving function, and the self-driving control module may refer to a software module or a chip implementing the software module by hardware. The self-driving control module may be included in the self-driving vehicle 100b as a component thereof, but may be implemented with separate hardware and connected to the outside of the self-driving vehicle 100b.

The self-driving vehicle 100b may acquire state information about the self-driving vehicle 100b by using sensor information acquired from various kinds of sensors, may detect (recognize) surrounding environment and objects, may generate map data, may determine the route and the travel plan, or may determine the operation.

Like the robot 100a, the self-driving vehicle 100b may use the sensor information acquired from at least one sensor among the lidar, the radar, and the camera so as to determine the travel route and the travel plan.

In particular, the self-driving vehicle 100b may recognize the environment or objects for an area covered by a field of view or an area over a certain distance by receiving the sensor information from external devices, or may receive directly recognized information from the external devices.

The self driving vehicle 100b may perform the above described operations by using the learning model composed of at least one artificial neural network. For example, the self-driving vehicle 100b may recognize the surrounding environment and the objects by using the learning model, and may determine the traveling movement line by using the recognized surrounding information or object information. The learning model may be learned directly from the self-driving vehicle 100a or may be learned from an external device such as the AI server 200.

At this time, the self-driving vehicle 100b may perform the operation by generating the result by directly using the learning model, but the sensor information may be transmitted to the external device such as the AI server 200 and the generated result may be received to perform the operation.

The self-driving vehicle 100b may use at least one of the map data, the object information detected from the sensor information, or the object information acquired from the external apparatus to determine the travel route and the travel plan, and may control the driving unit such that the self-driving vehicle 100b travels along the determined travel route and travel plan.

The map data may include object identification information about various objects arranged in the space (for example, road) in which the self-driving vehicle 100b travels. For example, the map data may include object identification information about fixed objects such as street lamps, rocks, and buildings and movable objects such as vehicles and pedestrians. The object identification information may include a name, a type, a distance, and a position.

In addition, the self-driving vehicle 100b may perform the operation or travel by controlling the driving unit based on the control/interaction of the user. At this time, the self-driving vehicle 100b may acquire the intention information of the interaction due to the user's operation or speech utterance, and may determine the response based on the acquired intention information, and may perform the operation.

<AI+XR>

The XR device 100c, to which the AI technology is applied, may be implemented by a head-mount display (HMD), a head-up display (HUD) provided in the vehicle, a television, a mobile phone, a smartphone, a computer, a wearable device, a home appliance, a digital signage, a vehicle, a fixed robot, a mobile robot, or the like.

The XR device 100c may analyzes three-dimensional point cloud data or image data acquired from various sensors or the external devices, generate position data and attribute data for the three-dimensional points, acquire information about the surrounding space or the real object, and render to output the XR object to be output. For example, the XR device 100c may output an XR object including the additional information about the recognized object in correspondence to the recognized object.

The XR device 100c may perform the above-described operations by using the learning model composed of at least one artificial neural network. For example, the XR device 100c may recognize the real object from the three-dimensional point cloud data or the image data by using the learning model, and may provide information corresponding to the recognized real object. The learning model may be directly learned from the XR device 100c, or may be learned from the external device such as the AI server 200.

At this time, the XR device 100c may perform the operation by generating the result by directly using the learning model, but the sensor information may be transmitted to the external device such as the AI server 200 and the generated result may be received to perform the operation.

<AI+Robot+Self-Driving>

The robot 100a, to which the AI technology and the self-driving technology are applied, may be implemented as a guide robot, a carrying robot, a cleaning robot, a wearable robot, an entertainment robot, a pet robot, an unmanned flying robot, or the like.

The robot 100a, to which the AI technology and the self-driving technology are applied, may refer to the robot itself having the self-driving function or the robot 100a interacting with the self-driving vehicle 100b.

The robot 100a having the self-driving function may collectively refer to a device that moves for itself along the given movement line without the user's control or moves for itself by determining the movement line by itself.

The robot 100a and the self-driving vehicle 100b having the self-driving function may use a common sensing method so as to determine at least one of the travel route or the travel plan. For example, the robot 100a and the self-driving vehicle 100b having the self-driving function may determine at least one of the travel route or the travel plan by using the information sensed through the lidar, the radar, and the camera.

The robot 100a that interacts with the self-driving vehicle 100b exists separately from the self-driving vehicle 100b and may perform operations interworking with the self-driving function of the self-driving vehicle 100b or interworking with the user who rides on the self-driving vehicle 100b.

At this time, the robot 100a interacting with the self-driving vehicle 100b may control or assist the self-driving function of the self-driving vehicle 100*b* by acquiring sensor information on behalf of the self-driving vehicle 100*b* and providing the sensor information to the self-driving vehicle 100*b*, or by acquiring sensor information, generating environment information or object information, and providing the information to the self-driving vehicle 100*b*.

Alternatively, the robot 100*a* interacting with the self-driving vehicle 100*b* may monitor the user boarding the self-driving vehicle 100*b*, or may control the function of the self-driving vehicle 100*b* through the interaction with the user. For example, when it is determined that the driver is in a drowsy state, the robot 100*a* may activate the self-driving function of the self-driving vehicle 100*b* or assist the control of the driving unit of the self-driving vehicle 100*b*. The function of the self-driving vehicle 100*b* controlled by the robot 100*a* may include not only the self-driving function but also the function provided by the navigation system or the audio system provided in the self-driving vehicle 100*b*.

Alternatively, the robot 100*a* that interacts with the self-driving vehicle 100*b* may provide information or assist the function to the self-driving vehicle 100*b* outside the self-driving vehicle 100*b*. For example, the robot 100*a* may provide traffic information including signal information and the like, such as a smart signal, to the self-driving vehicle 100*b*, and automatically connect an electric charger to a charging port by interacting with the self-driving vehicle 100*b* like an automatic electric charger of an electric vehicle.

<AI+Robot+XR>

The robot 100*a*, to which the AI technology and the XR technology are applied, may be implemented as a guide robot, a carrying robot, a cleaning robot, a wearable robot, an entertainment robot, a pet robot, an unmanned flying robot, a drone, or the like.

The robot 100*a*, to which the XR technology is applied, may refer to a robot that is subjected to control/interaction in an XR image. In this case, the robot 100*a* may be separated from the XR device 100*c* and interwork with each other.

When the robot 100*a*, which is subjected to control/interaction in the XR image, may acquire the sensor information from the sensors including the camera, the robot 100*a* or the XR device 100*c* may generate the XR image based on the sensor information, and the XR device 100*c* may output the generated XR image. The robot 100*a* may operate based on the control signal input through the XR device 100*c* or the user's interaction.

For example, the user can confirm the XR image corresponding to the time point of the robot 100*a* interworking remotely through the external device such as the XR device 100*c*, adjust the self-driving travel path of the robot 100*a* through interaction, control the operation or driving, or confirm the information about the surrounding object.

<AI+Self-Driving+XR>

The self-driving vehicle 100*b*, to which the AI technology and the XR technology are applied, may be implemented as a mobile robot, a vehicle, an unmanned flying vehicle, or the like.

The self-driving driving vehicle 100*b*, to which the XR technology is applied, may refer to a self-driving vehicle having a means for providing an XR image or a self-driving vehicle that is subjected to control/interaction in an XR image. Particularly, the self-driving vehicle 100*b* that is subjected to control/interaction in the XR image may be distinguished from the XR device 100*c* and interwork with each other.

The self-driving vehicle 100*b* having the means for providing the XR image may acquire the sensor information from the sensors including the camera and output the generated XR image based on the acquired sensor information. For example, the self-driving vehicle 100*b* may include an HUD to output an XR image, thereby providing a passenger with a real object or an XR object corresponding to an object in the screen.

At this time, when the XR object is output to the HUD, at least part of the XR object may be outputted so as to overlap the actual object to which the passenger's gaze is directed. Meanwhile, when the XR object is output to the display provided in the self-driving vehicle 100*b*, at least part of the XR object may be output so as to overlap the object in the screen. For example, the self-driving vehicle 100*b* may output XR objects corresponding to objects such as a lane, another vehicle, a traffic light, a traffic sign, a two-wheeled vehicle, a pedestrian, a building, and the like.

When the self-driving vehicle 100*b*, which is subjected to control/interaction in the XR image, may acquire the sensor information from the sensors including the camera, the self-driving vehicle 100*b* or the XR device 100*c* may generate the XR image based on the sensor information, and the XR device 100*c* may output the generated XR image. The self-driving vehicle 100*b* may operate based on the control signal input through the external device such as the XR device 100*c* or the user's interaction.

Figure 4:
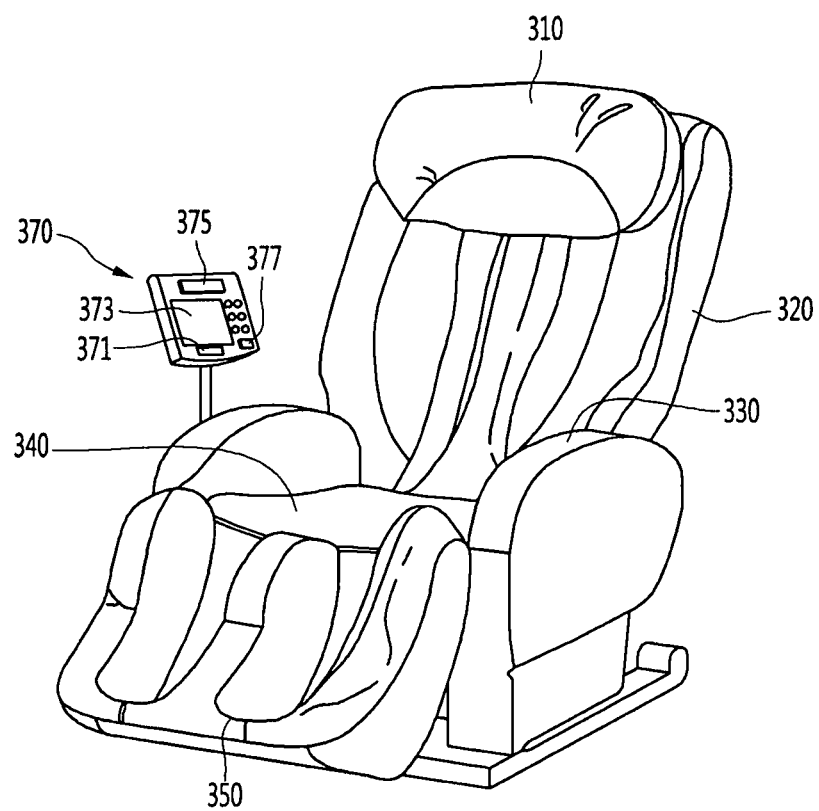
FIG. 4 is a perspective view for explanation of a configuration of the massage chair according to an embodiment of the present invention.

FIG. 4 is a perspective view for explanation of a configuration of the massage chair 300 according to an embodiment of the present invention.

The massage chair 300 may be used together with the AI device 100 illustrated in FIG. 1.

The massage chair 300 may include at least one of the head massage unit 310 configured to support the user head, the back massage unit 320 configured to the user back, the arm massage unit 330 configured to the user arm, the buttocks massage unit 340 configured to support the user buttocks, or the leg massage unit 350 configured to support the user leg.

Each of the head massage unit 310, the back massage unit 320, the arm massage unit 330, the buttocks massage unit 340 and the leg massage unit 350 may be driven by a driving unit (not shown) to be rotated or moved. For example, by rotating the back massage unit 320 upwards by the driver, the user sitting on the back massage unit 320 may be maintained in an oblique posture or a 90 degree-vertical posture. For example, by rotating the back massage unit 320 downwards by the driver, the user sitting on the back massage unit 320 may be maintained in a horizontal posture.

Each of the head massage unit 310, the back massage unit 320, the arm massage unit 330, the buttocks massage unit 340, and the leg massage unit 350 may include one or more rollers or one or more massage sticks, and may perform a preset operation using the force transmitted from the driver 220 to perform massage.

Each of the head massage unit 310, the back massage unit 320, the arm massage unit 330, the buttocks massage unit 340, and the leg massage unit 350 may include an airbag. An air pressure of the airbag included in each of the head massage unit 310, the back massage unit 320, the arm massage unit 330, the buttocks massage unit 340, and the leg massage unit 350 may be adjusted, and thus massage with various intensities may be provided to the user.

The massage chair 300 may include a support that configures a structure of the inside of the massage chair 300.

The entire portion of the massage chair 300 may be rotated in left and right or upward and downward directions by the force transmitted from the driver 220.

The massage chair 300 may include an operating unit 370. The operating unit 370 may include the driving unit (not shown). The operating unit 370 may be rotated or moved by the driving unit.

The operating unit 370 may include a microphone 371, a camera 375, a button, a display unit 373, a speaker 377, and so forth. Herein, the microphone 371, the camera 375 and the button may be included in the input unit 120 illustrated in FIG. 1. The display unit 373 and the speaker 377 may be included in the output unit 150 illustrated in FIG. 1. The operating unit 370 may include more or less components than that described herein.

For example, the operating unit 370 may be installed in a distance that the user's arm may reach. As an example, the operating unit 370 may be installed in one side of the arm massage unit 330.

For example, if there is no need for an operation of the user, the operating unit 370 may be installed in front of the user. In this case, a command related to the massage chair 300 or other related command may be recognized by using the user's utterance, and its corresponding follow-up steps may be performed.

The microphone 371 may receive the user's utterance. The massage chair 300 may be controlled by the user's utterance. The camera 375 may receive a face image of the user. For example, the processor 180 may control the display unit 373 to be moved toward the user's face based on the face image of the user. The button may be used in receiving the command of the user or receiving a text.

The display unit 373 may display information. The information may include a manual of the massage chair 300, information related to the massage chair 300, and a content concerning a massage-related image. The information may include surfing information via the Internet network. The information may include contents such as a broadcast, a movie or the like. The speaker 377 may output an audio related to information displayed on the display unit 375. The speaker 377 may output a variety of audios that should be transmitted to the user. For example, the corresponding audio may include schedule notification, completion notification of operation of household appliances, destination arrival notification or an appointment schedule notification, wake-up notification and a voice message, but the present invention is not limited thereto.

Each of the head massage unit 310, the back massage unit 320, the arm massage unit 330, the buttocks massage unit 340, and the leg massage unit 350 may include one or more low-ranking massage devices. For example, the head massage unit 310 may include at least one of a head massage device configured to perform massage on the user head, or a neck massage device configured to perform massage on the user neck. In another example, the back massage unit 320 may include at least one a shoulder massage device configured to perform massage on the user shoulder, a shoulder massage device configured to perform massage on the user back, and a back massage device configured to perform massage on the user waist. In another example, the leg massage unit 350 may include at least one of a thigh massage device configured to perform massage on the user thigh, a calf massage device configured to perform massage on the user calf, or a foot massage device configured to perform massage on the user foot.

Although the configuration and operation method of the massage chair 300 have been described above, the present invention is not limited to the aforementioned massage chair 300. In detail, various documents disclose the configuration and operation method of the massage chair, and the massage chair 300 according to an embodiment of the present invention may be applied various known types of massage chairs.

Meanwhile, the message chair of the present invention may communicate with another device via 5G communication or a 5G network. For example, data or information created in the massage chair of the present invention may be stored in a server via the 5G communication or the 5G network, or data or information may be received from the corresponding server via the 5G communication or the 5G network. For example, the massage chair of the present invention may control another device via the 5G communication or the 5G network, or may be controlled by another device via the 5G communication or the 5G network.

Figure 5:
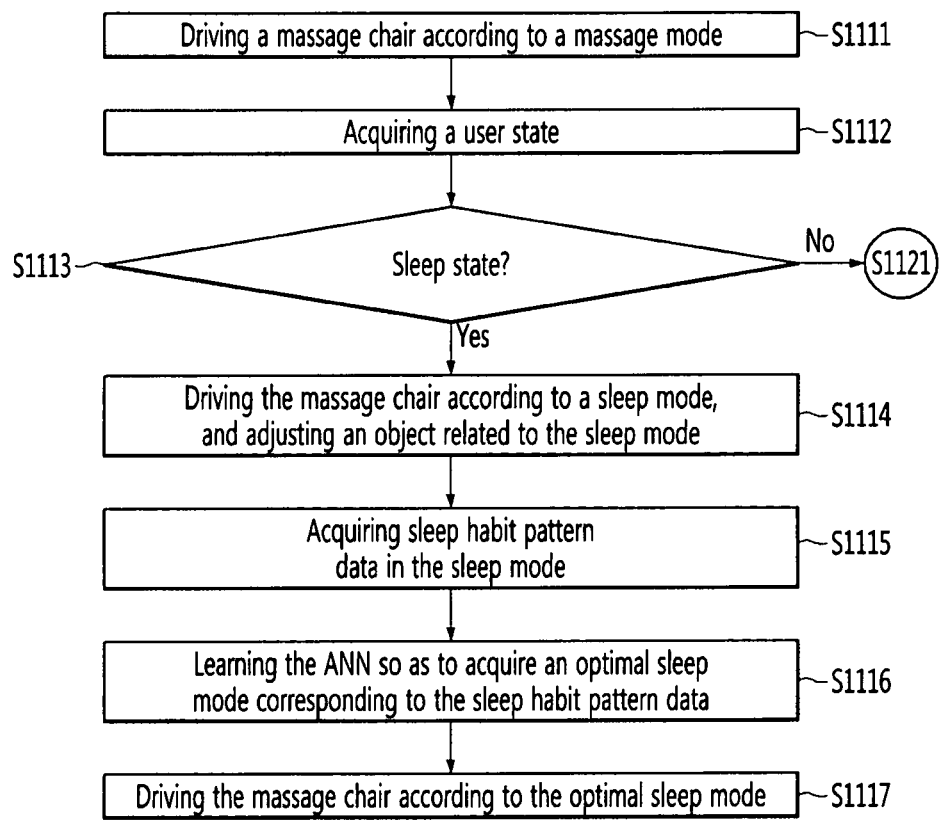
FIG. 5 is a flowchart for explanation of a method for driving the massage chair in a sleep mode according to an embodiment of the present invention.
Figure 6:
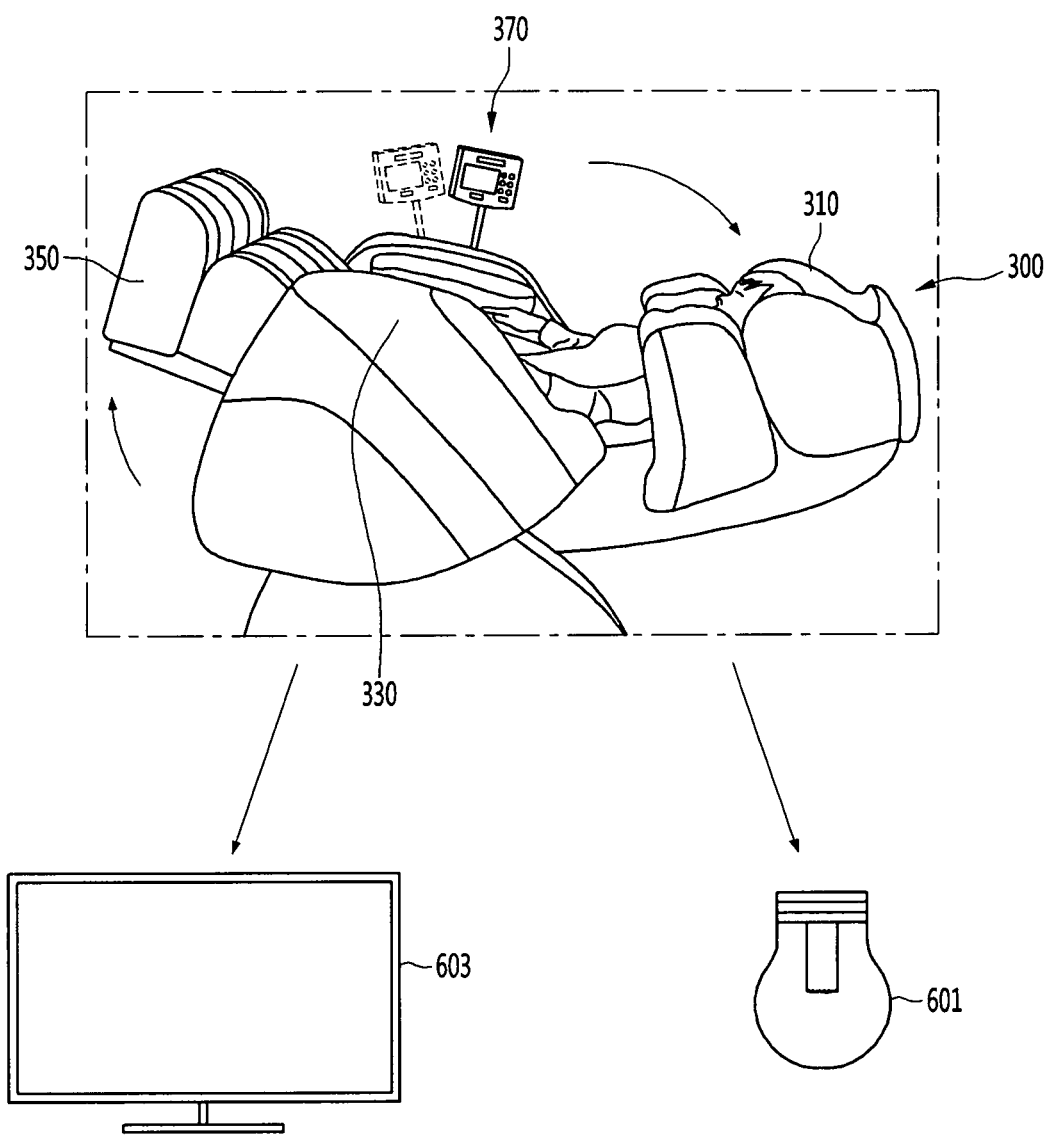
FIG. 6 is an exemplary view showing a method for driving the massage chair in a sleep mode according to an embodiment of the present invention.

Referring to FIGS. 5 and 6 below, an operating method of the massage chair in a sleep mode will be described.

FIG. 5 is a flowchart for explanation of a method for driving the massage chair in a sleep mode according to an embodiment of the present invention.

Referring to FIGS. 1, 4 and 5, the processor 180 may control the massage chair 300 to be driven according to a massage mode (S1111).

When a command of selecting the massage mode is received from the user sitting on the massage chair 300, the processor 180 may drive the driving chair 300 based on massage mode-related information preset according to the corresponding massage mode. The massage mode and the massage mode-related information may be stored in the memory 170. For example, the massage mode-related information may include rotation information, vibrational intensity information, massage operation time information and the like so as to rotate at least one of the head massage unit 310, the back massage unit 320, the arm massage unit 330, the buttocks massage unit 340, and the leg massage unit 350. The massage mode-related information may be modified or newly set.

The massage mode may include at least one massage mode, and the massage mode-related information of each of these massage modes may be different from one another. The massage chair 300 may be driven according to the massage mode selected among these massage modes.

Although not shown in this figure, when the user sits on the massage chair 300, the processor 180 may acquire whether a corresponding user is a user who previously registered his/her fingerprint by recognizing the user's fingerprint. When the user is not the user who previously registered the user's fingerprint, the processor 180 may control the display unit 373 to display user fingerprint registration guide information. When the fingerprint is received from the user in response to the corresponding user fingerprint registration guide information, the processor 180 may store the received fingerprint in the memory 170. When the corresponding user is a user who cannot use the corresponding massage chair 300, the processor 180 may control the display unit 373 to display an unserviceable message.

In addition, the processor 180 may control a sensing unit so as to receive information such as a user's temperature, blood pressure, body fat, and the like. The information such as the user's temperature, blood pressure, body fat, and the like, may be received whenever the user sits on the massage chair 300, or by periods. When the body information of the user is received, the processor 180 may receive the body information of the corresponding user and store the body information in the memory 170. The user body information may include, for example, height, weight, gender, age, and the like. The user body information may be stored to correspond to an identifier of the corresponding user. The body information of the user may be stored in the memory 170 via a registration process.

The processor 180 may receive a user state (S1112).

For example, the user state may be a sleep mode that the user has a good sleep, or a wake-up mode that the user wakes up from the sleep state, but the present invention is not limited thereto. For example, the sleep state may be determined based on a temperature, blood pressure and a breathing sound (or a snoring sound), which were received from the user. For example, the wake-up state may be determined based on a preset event or a sound according to a stretch of the user. The preset event, for example, may include at least one of schedule notification, completion notification of operation of household appliances, destination arrival notification or appointment schedule notification. The preset event, for example, may include at least one of a wake-up notification, a voice message and a content having a sound. The content having the sound, for example, may include music or an image played at a previously set time, but the present invention is not limited thereto.

The processor 180 may receive whether the user state has the sleep state (S1113).

The processor 180, for example, may receive whether the user state has the sleep state, based on the user's breathing sound or snoring sound, as well as the temperature and blood pressure received from the user. When the breathing sound or the snoring sound is received via a microphone while the user sitting on the massage chair 300 gets a massage, the processor 180 may receive whether the user state has the sleep state, based on the user's temperature or blood pressure previously received, in addition to such sounds. A table indicating a relation between the sleep states and a temperature, blood pressure, a breathing sound and the like, may be previously stored in the memory 170. Accordingly, the processor 180 may receive whether the user state has the sleep state, by referring to the table stored in the memory 170 based on the temperature, the blood pressure and the breathing sound received from the user.

The processor 180 may control the massage chair 300 to be driven according to the sleep mode (S1114).

The processor 180 may adjust an object related to the sleep mode. The adjustment of the object related to the sleep mode may be performed simultaneously with the driving of the massage chair 300 according to the sleep mode. In addition, the adjustment of the object related to the sleep mode may be performed before or after driving the massage chair 300 according to the sleep mode. For example, after driving the massage chair 300 according to the sleep mode, the object related to the sleep mode may be adjusted after a few seconds.

The object related to the sleep mode may mean a target that may interrupt the user's sleep so that the user may maintain the sleep state consistently or pleasantly. For example, the object related to the sleep mode may include electronic equipment and the like, such as a lamp, a currently driven television, an audio device and a washing machine. For example, the object related to the sleep mode may include a window that may connect or interrupt the outside. For example, when the window is open to be connected to the outside, the user's sleep may be interrupted by a sound created from the outside. In this case, the processor 180 may control the window to be closed so as to cut off the outside.

As illustrated in FIG. 6, when a lamp 601 is turned on, brightness of the lamp 601 may be reduced or the lamp 601 may be turned off. For example, when a television 603 is turned on, the television 603 may be allowed to be turned off, or the sound of the television 603 may be allowed not to be outputted. For example, when the washing machine is in operation, the operation of the washing machine may be temporarily stopped, or the washing machine may not be turned off. For example, the temperature may be adjusted to a temperature that helps the user's sleep. For example, since the user may feel chilly when the user sleeps, the temperature may be adjusted to increase more by 1 degree to 5 degrees than before. In addition to this, the motion and the like of a target that interrupts the user's sleep may be adjusted to improve comfortability of the user's sleep.

For example, the processor 180 may drive the massage chair 300 horizontally so as to maintain a state similar to when the user sleeps, according to the sleep mode, as illustrated in FIG. 6. For example, the back massage unit 320 and the leg massage unit 350 may match with each other in a horizontal direction by rotating the back massage unit 320 downwards and rotating the leg massage unit 350 upwards.

Meanwhile, the user may sleep on the massage chair 300 driven according to the sleep mode, and may take specific motions during sleep. For example, the user may have a sleep without any movement, the user may take a twisting motion in order to change to a reclining posture, or the user may frequently move his/her arms up and down without being consistently maintained in one place. As described above, a sleep habit occurring when the user sleeps may be received.

The processor 180 may receive sleep habit pattern data in the sleep mode (S1115).

For example, the processor 180 may receive the sleep habit pattern data of the user by using a microphone, and the camera 375, and the like. Whenever the user has a sleep in the massage chair 300, the sleep habit pattern data of the user may be received.

The processor 180 may receive the ANN so as to acquire an optimal sleep mode corresponding to the sleep habit pattern data (S1116).

The processor 180 may receive the optimal sleep mode by learning the received sleep habit pattern data by using the ANN. By learning the sleep habit pattern received whenever the user sleeps, the sleep mode may be upgraded to receive the optimal sleep mode that may provide comfortability to the user's good sleep. The optimal sleep mode may be received by following a target value (or a line). That is, when a value of the sleep mode received from the ANN has a difference (a gap) from a value of a target sleep mode, the ANN may learn to reduce the difference, thus receiving the optimal sleep mode.

The processor 180 may drive the massage chair 300 according to the optimal sleep mode (S1117).

The processor 180 may provide the best comfortability such that the user may have a good sleep, by driving the massage chair 300 according to the optimal sleep mode received by the ANN. A posture of the massage chair 300 may be changed according to the sleep mode and the massage mode. For this, rotational values of each massage unit 310 to 350 of the massage unit 300 may be changed according to the sleep mode and the massage mode.

In accordance with an embodiment of the present invention, when the massage chair 300 recognizes the user's sleep during operation in the massage mode, the massage mode may be changed to the sleep mode to operate the massage chair 300, and the massage chair 300 may be allowed to operate in the optimal sleep mode by learning the sleep habit pattern data received during sleep, thus ensuring the sleep comfortability of the user and improving the user's convenience. In particular, according to an embodiment of the present invention, the sleep pattern data of the user is learned by the ANN, and thus the best sleep comfortability may be provided to the user not via an operating of the massage chair 300 according to a fixed sleep mode but via an operation of the massage chair 300 according to a consistently upgraded sleep mode.

Hereinafter, referring to FIGS. 7 and 8, a method for changing from the massage mode to the sleep mode will be described.

Figure 7:
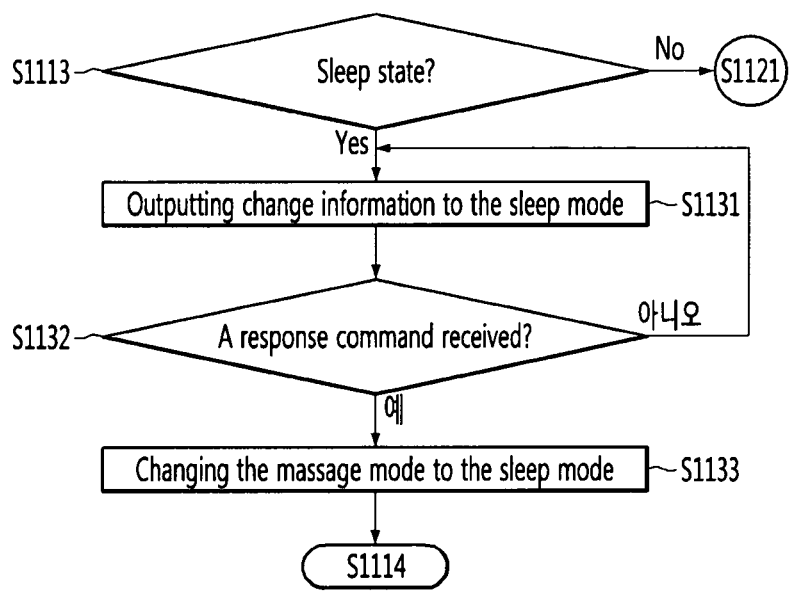
FIG. 7 is a flowchart for explanation of a method for changing to a sleep mode according to an embodiment of the present invention.
Figure 8:
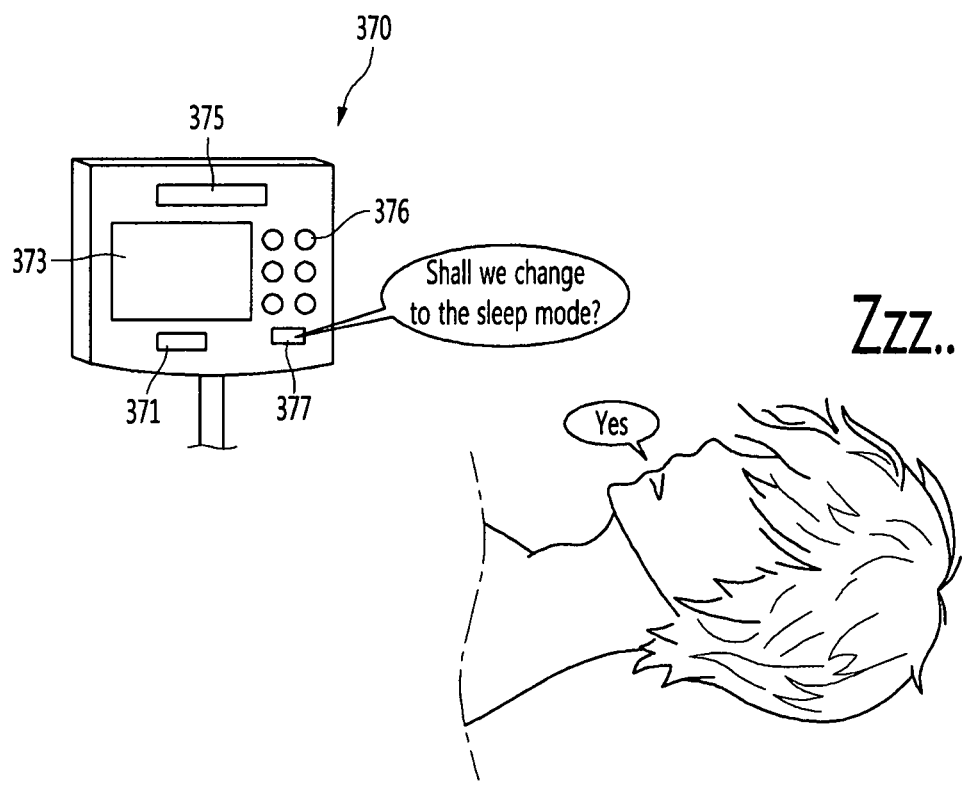
FIG. 8 is an exemplary view explaining a method for changing to a sleep mode according to an embodiment of the present invention.

FIG. 7 is a flowchart for explanation of a method for changing to a sleep mode according to an embodiment of the present invention. FIG. 7 may illustrate the operation performed between the steps S1113 and S1114 illustrated in FIG. 5.

Referring to FIGS. 1, 4, 5 and 7, the processor 180 may output change information to the sleep mode (S1131).

For example, the change information to the sleep mode may be outputted with a text. For example, the processor 180 may control the display unit 373 to display the change information to the sleep mode. For example, the text "Shall we change to the sleep mode?" may be displayed on a screen of the display unit 373. For example, the change information to the sleep mode may be outputted with a voice. For example, the processor 180 may control the speaker 377 to output the change information to the sleep mode. As illustrated in FIG. 8, the voice "Shall we change to the sleep mode?" may be outputted with a sound via the speaker 377.

The processor 180 may receive whether a response command is received (S1132).

The response command may be created by a text input or a button click. The processor 180 may determine whether the corresponding text is the response command by receiving the text inputted via the input unit. The response command may be created by an utterance. As illustrated in FIG. 8, the voice "Yes" is inputted from the user via the microphone, and the processor 180 may determine whether the corresponding voice is the response command by receiving the voice of the user.

A non-response of the user may be also a command of requesting a change to the sleep mode. For example, when utterance information is not received from the user during a predetermined time, the processor 180 may determine that the user requests a change to the sleep mode. For example, the predetermined time is three seconds, but the present invention is not limited thereto. In another example, when the utterance information corresponding to the response command is not received from the user, the processor 180 may determine a final response command of the user through whether the response command of the user is received, by outputting change information to the sleep mode at least two times. For example, when the utterance information corresponding to the response command is not received from the user, the processor 180 may output the change to the sleep mode three times, but the present invention is not limited thereto.

The processor 180 may change the massage mode to the sleep mode (S1133).

When the response command, i.e., a command of changing to the sleep mode, is received, the processor 180 may change the massage mode to the sleep mode. The processor 180 may control the massage chair 300 previously operated to the massage mode according to the sleep mode changed like this to be operated according to the sleep mode.

Hereinafter, referring to FIG. 9, a method for changing from the sleep mode to the wake-up mode will be described.

Figure 9:
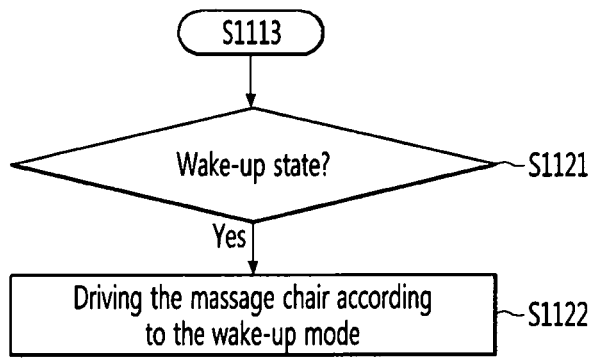
FIG. 9 is a flowchart for explanation of a method for driving the massage chair in a wake-up mode according to an embodiment of the present invention.

FIG. 9 is a flowchart for explanation of a method for driving the massage chair in a wake-up mode according to an embodiment of the present invention. FIG. 9 may illustrate an operation corresponding to the case that the user state does not have the sleep state in the sleep state determination step (S1113) shown in FIG. 5.

Referring to FIGS. 1, 4, 5 and 9, the processor 180 may receive whether the user state has the wake-up state (S1121).

The wake-up state may be acquired when an event satisfying a previous condition occurs. For example, the event may include schedule notification, completion notification of operation of household appliances, destination arrival notification, appointment schedule notification, and so forth. For example, such an event may be outputted with a voice via the speaker 377, but the present invention is not limited thereto.

For example, the schedule notification may be outputted with the voice "Sir, please get up. You have to go to lecture at 2 p.m.".

For example, the completion notification of operation of household appliances may be outputted with the voice "The laundry has been washed. The laundry may smell, so please take it out as soon as possible.".

For example, the destination arrival notification corresponds to the case that the massage chair 300 is mounted in a moving object such as a vehicle, and a seat of the vehicle may include a function of the massage chair 300 described in an embodiment of the present invention. In this case, the destination arrival notification may be outputted with the voice "Sir, please get up now. You arrived at the destination".

For example, the appointment schedule notification is to guide an appointment schedule with, for example, friends or customers, and may be outputted with the voice "You have an appointment with a customer at 3 p.m.".

In addition to this, an event of satisfying a situation or an environment that the user in sleep should get up may also be included in the embodiment of the present invention.

Meanwhile, the wake-up state may be acquired when set information is outputted. The set information may include a wake-up notification, a voice massage, a content having a sound, and the like. The wake-up notification is a predetermined wake-up time, and may be a time set after the user goes to sleep. For example, when the wake-up time is set to 30 minutes, the wake-up notification will be outputted in 30 minutes after the user goes to sleep. The voice message may be created as the voice "Please wake up", for example, in various forms such as a dialect version, a rap version, or the like. The content having the sound may be outputted with a set music and/or image, for example, when the set wake-up time comes.

The processor 180 may control the massage chair 300 to be driven according to the wake-up mode (S1122).

When occurrence of the corresponding event is received, the processor 180 may change the sleep mode to the wake-up mode, and may drive the massage chair 300 according to the changed wake-up mode. That is, the processor 180 may restore a posture of the massage chair 300 back again. The processor 180 may force the user to wake up by shaking of the massage chair 300 by endowing strong vibration to the massage chair 300 in order to wake up the user in sleep.

In addition, the processor 180 may control the previously adjusted object to be restored back again. For example, the processor 180 may turn on the lamp again, turn on the television again, and operate the washing machine temporarily stopped. In addition, the processor 180 may open a closed window. The processor 180 may confirm the outside weather before opening the closed window, and may open the window when it does not rain, and keep the window closed, when it rains.

According to an embodiment of the present invention, when the wake-up time comes, the user may be forced to wake up to help the user not to lose his/her schedule.

Hereinafter, referring to FIGS. 10 and 11, a method for adjusting the display unit according to the movement of the user will be described.

Figure 10:
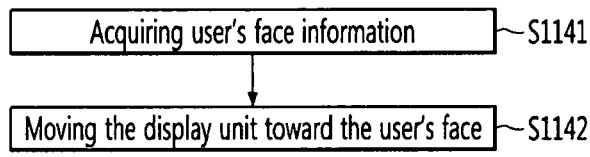
FIG. 10 is a flowchart for explanation of a method for moving a display unit based on a face of a user according to an embodiment of the present invention.

FIG. 10 is a flowchart for explanation of a method for moving a display unit based on a face of a user according to an embodiment of the present invention.

Referring to FIGS. 1, 4 and 10, the processor 180 may acquire user's face information (S1141).

The camera 375 may capture the face of the user. The processor 180 may acquire the face information based on the face of the user captured via the camera 375.

The processor 180 may control the display unit 373 to be moved toward the face of the user (S1142).

The processor 180 may receive a distance between the face of the user and the display unit 373 based on the face information of the user. The processor 180 may receive the user's eyes based on the face information of the user. The processor 180 may control the display unit 373 to be moved based on a corresponding distance and/or a location of eyes. That is, the movement of the display unit 373 may include, for example, rotation, inclination, displacement and the like. For example, the rotation may mean an up and down movement forwards and backwards based on a shaft. The inclination may mean an up and down movement left and right. The displacement may mean a movement such that the display unit 373 approaches the user or moves away from the user.

Figure 11A:
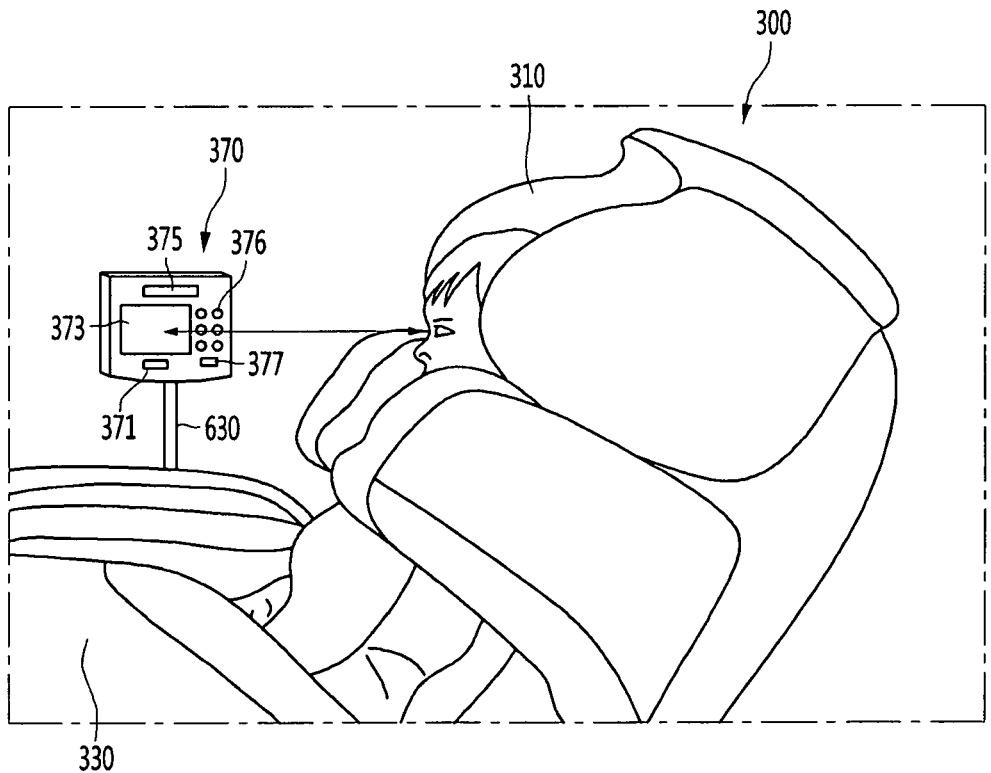
FIGS. 11a and 11b are exemplary views showing a method for moving a display unit according to when a user sits or lies down.

As illustrated in FIG. 11a, when the user sits on the massage chair 300 in a normal state, the user may sit on the massage chair 300 in a 90 degree-vertical posture or an oblique posture. In this case, the processor 180 may acquire the face information of the user via the camera 375, and control the display unit 373 to be moved toward the face of the user based on the acquired face information. That is, the processor 180 may control the display unit 373 such that a screen of the display unit 373 is moved from a forward and backward direction to the up and down direction or moved from a left and right direction to the up and down direction to be perpendicular or oblique to the eyes of the user.

Figure 11B:
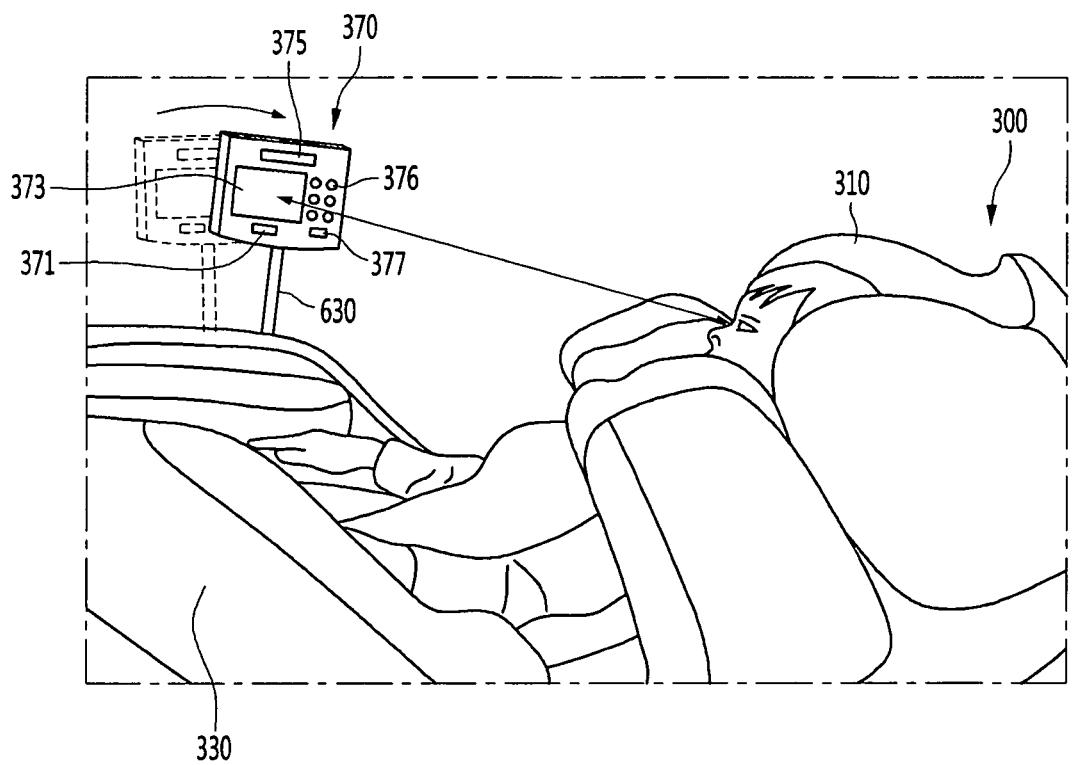

As illustrated in FIG. 11b, in a specific situation, for example, the case that the massage chair 300 is horizontally driven by the sleep mode and the user is also maintained in a horizontal posture or an oblique posture, the face or eyes of the user may face upwards. Accordingly, the processor 180 may control the display unit 373 to face the face of the user. That is, the display 180 may allow a support 630 of the display unit 373 to be extended upwards and allow the display unit 373 to be moved from a front direction to an upward direction. Accordingly, the display unit 373 may approach the face of the user, and the display unit 373 may face the face of the user.

According to an embodiment of the present invention, the display unit 373 may control its displacement to always face the user or be positioned around the user, by which the user may enjoy or conveniently use information displayed on the display unit 373. In addition, by moving the microphone 371 around the user along with the display unit 373, the utterance of the user may be easily recognized to prevent malfunction caused by recognition faults.

Hereinafter, referring to FIG. 12, a method for reconfigurating an icon according to a body characteristic of the user will be described.

Figure 12:
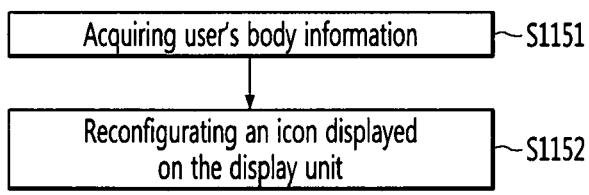
FIG. 12 is a flowchart for explanation of a method for reconfigurating an icon displayed on a display unit according to a body characteristic of a user.

FIG. 12 is a flowchart for explanation of a method for reconfigurating an icon displayed on a display unit according to a body characteristic of a user.

Referring to FIGS. 1, 4 and 12, when the user sits on the massage chair 300, the processor 180 may receive body information (S1151). For example, the user body information may include height, weight, gender, age, and the like. The user body information may be stored to correspond to an identifier of the corresponding user.

The processor 180 may reconfigurate an icon displayed on the display unit 373 (S1152). The word 'reconfigurate' is substituted as the word 'rearrange' or the word 'reconstitute'.

A variety of executable icons may be displayed on the display unit 373. Since such icons are set by a previously fixed font or size, the icons are displayed on the display unit 373 regardless of the body information of the user. Hence, for example, users with bad eyesight or old people have difficult in seeing the corresponding icons.

According to an embodiment of the present invention, for example, when the users are old people, the icon may be reconfigurated so as to adjust the font of the icon or expend the size of the icon.

For example, the processor 180 may control the movement of the display unit 373 such that a distance between the user and the display unit 373 is changed based on the body information of the user. For example, the display unit 373 may be moved toward the user such that the older the user is, the closer the display unit 373 comes to the user.

For example, the processor 180 may control the movement of the display unit 373 as well as reconfigurate the icon based on the body information of the user.

According to an embodiment of the present invention, the convenience of the user may be improved by providing an icon having a size suitable for the user.

Hereinafter, referring to FIG. 13, a massage driving method after finishing the massage will be described.

Figure 13:
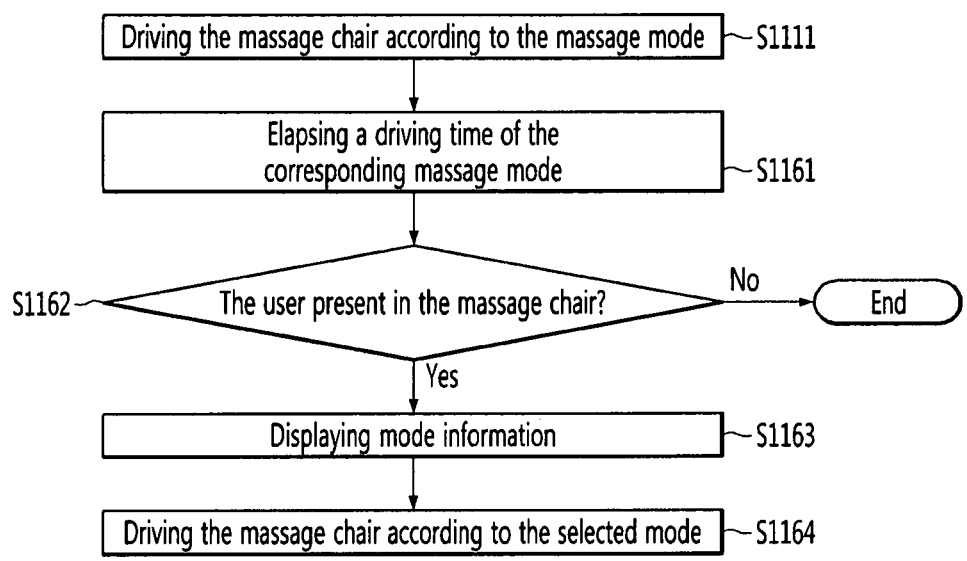
FIG. 13 is a flowchart for explanation of a massage driving method in the case that a user does not deviate after finishing massage.

FIG. 13 is a flowchart for explanation of a massage driving method in the case that a user does not deviate after finishing massage.

Referring to FIGS. 1, 4 and 12, the processor 180 may control the massage chair 300 to be driven according to the massage mode (S1111). Since the step S1111 has been already described in FIG. 5, overlapping descriptions for those are omitted.

The processor 180 may receive whether a driving time of the corresponding massage mode elapsed (S1161). The massage mode may drive the massage chair during a preset time. When the preset time elapses, the driving of the massage chair may be finished.

The processor 180 may receive whether the user still sits on the massage chair (S1162). The processor 180 may receive whether the user keeps sitting after the preset time elapse. For example, a weight sensing sensor is installed on the buttocks massage unit 340. The weight sensing sensor may sense whether the user keeps sitting. For example, when the user is sitting, the weight sensing sensor may transmit a high level, i.e., a signal of "1", to the processor 180, and the processor 180 may receive that the user is setting on the massage chair, based on a high level signal received from the weight sensing sensor. For example, when the user deviates from the massage chair 300, the weight sensing sensor may transmit a low level, i.e., a signal of "0", to the processor 180, and the processor 180 may receive that the user is not present on the massage chair, based on a low level signal received from the weight sensing sensor.

Figure 14:
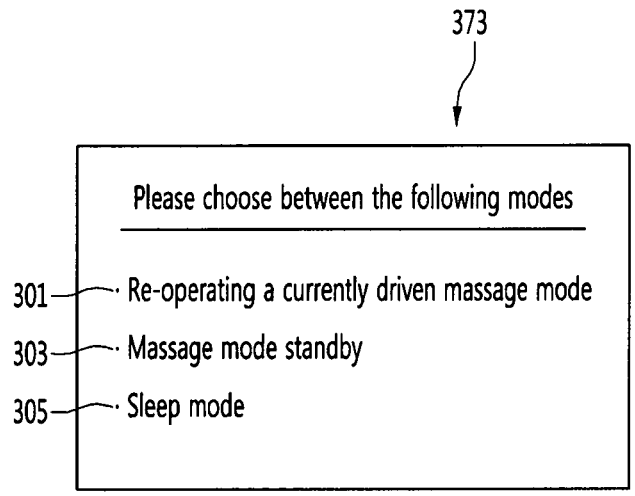
FIG. 14 illustrate mode information on a display unit.

Although the preset time elapses, when the user sits in the massage chair, the processor 180 may control mode information to be displayed on the display unit 373 (S1163). The mode information may be displayed on the display unit 373, as illustrated in FIG. 14. For example, a currently driven massage mode re-operation 301, a massage mode standby 303 and a sleep mode 305, as mode information, may be displayed on the display unit 373.

The processor 180 may control the massage chair to be driven according to a mode which the user selects among the mode information (S1164).

For example, when a command of selecting the currently driven massage mode 301 is received, the processor 180 may drive the massage chair back in a massage mode driven a while ago. Although not shown, one side of the currently driven massage mode 301 may display at least one number selection key. For example, the number selection keys such as one time, two times, three times, five times and the like, may be displayed on the display unit 373. When the command of selecting the corresponding number selection key is received, the processor 180 may control the massage chair to be driven by the selected number.

For example, when the command of selecting the massage mode standby 303 is received, the processor 180 may keep the massage chair intact in a state of closing the driving of the massage chair a while ago.

For example, when the command of selecting the sleep mode 305 is received, the processor 180 may control the massage chair to be driven according to the sleep mode. The driving of the massage chair in the sleep mode was already described in the step S1117 of FIG. 5. Hence, overlapping descriptions are omitted.

In accordance with an embodiment of the present invention, when the user does not deviate from the massage chair after getting massage in the massage mode, the user's convenience can be improved by providing the user with a function that can be additionally performed.

Therefore, in all aspect, the detailed description of the present disclosure is intended to be understood and interpreted as an exemplary embodiment of the present invention without limitation. The scope of the embodiment shall be decided based upon a reasonable interpretation of the appended claims of the present invention and all modifications in the scope of equivalents of the embodiment shall be included in the scope of the embodiment.

What is claimed is:

1. An operating method of a massage chair, the method comprising:
    driving the massage chair according to a massage mode;
    acquiring a user state;
    when the user state has a sleep state, changing the massage mode to a sleep mode and driving the massage chair according to the sleep mode, and controlling an object that interrupts a user's sleep to be adjusted to maintain the sleep state consistently;
    receiving a sleep habit pattern data of the user whenever the user is in the sleep state in the massage chair;
    driving the massage chair according to an optimal sleep mode by learning an artificial neural network (ANN) so as to acquire the optimal sleep mode corresponding to sleep habit pattern data in the sleep mode;
    obtaining face information of the user from a camera while horizontally driving the massage chair according to the sleep mode;
    obtaining a distance between a face of the user and a display unit based on the face information of the user; and
    moving the display unit and a microphone simultaneously to be adjacent to the face of the user based on the distance between the face of the user and the display unit,
    wherein the display unit and the microphone move until they face the face of the user.

2. The operating method of claim 1, further comprising:
    when the user state has the sleep state, outputting change information to the sleep mode; and
    when a command in response to the outputted change information to the sleep mode is received, changing to the sleep mode.

3. The operating method of claim 2, wherein at least one of the change information or the command is obtained based on an utterance.

4. The operating method of claim 1, when the user state has a wake-up state, changing the sleep mode to a wake-up mode and driving the massage chair according to the wake-up mode.

5. The operating method of claim 4, wherein the wake-up state is acquired when an event satisfying a predetermined condition occurs.

6. The operating method of claim 5, wherein the event includes at least one of schedule notification, completion notification of operation of household appliances, destination arrival notification or appointment schedule notification.

7. The operating method of claim 4, wherein the wake-up state is acquired when set information is outputted.

8. The operating method of claim 7, wherein the set information includes at least one of wake-up notification, a voice message or a content having a sound.

9. The operating method of claim 1, further comprising:
    acquiring body information of the user; and
    controlling an icon displayed on the display unit to be reconfigurable based on the acquired body information of the user.

10. The operating method of claim 1, further comprising:
    when the user does not deviate after finishing a fixed time of massage according to the massage mode, controlling mode information to be displayed on the display unit; and
    driving the massage chair according to a mode selected based on the mode information.

11. A massage chair, comprising:
    a camera;
    a display unit;
    a microphone;
    an artificial neural network (ANN); and
    a processor,
    wherein the processor is configured to:
        drive the massage chair according to a massage mode;
        acquire a user state;
        when the user state has a sleep state, change the massage mode to a sleep mode and drive the massage chair according to the sleep mode, and control an object that interrupts a user's sleep to be adjusted to maintain the sleep state consistently;
        receive a sleep habit pattern data of the user whenever the user is in the sleep state in the massage chair;
        drive the massage chair according to an optimal sleep mode by learning the ANN so as to acquire the optimal sleep mode corresponding to sleep habit pattern data in the sleep mode;
        obtain face information of the user from the camera while horizontally driving the massage chair according to the sleep mode;

obtain a distance between a face of the user and the display unit based on the face information of the user; and move the display unit and the microphone simultaneously to be adjacent to the face of the user based on the distance between the face of the user and the display unit, wherein the display unit and the microphone move until they face the face of the user.

12. The massage chair of claim 11, wherein the processor is configured to:

when the user state has the sleep state, output change information to the sleep mode; and when a command in response to the change information to the sleep mode is received, change to the sleep mode.

13. A vehicle including the massage chair of claim 12.

14. The massage chair of claim 11, wherein the processor is configured to:

when the user state is a wake-up state, change the sleep mode to a wake-up mode and drive the massage chair according to the wake-up mode.

15. A vehicle including the massage chair of claim 14.

16. The massage chair of claim 11, wherein the processor is configured to:

acquire body information of the user; and control an icon displayed on the display unit to be reconfigurable based on the acquired body information of the user.

17. The massage chair of claim 11, wherein the processor is configured to:

when the user does not deviate after finishing a fixed time of massage according to the massage mode, control mode information to be displayed on the display unit; and drive the massage chair according to a mode selected based on the mode information.

18. A vehicle including the massage chair of claim 11.

* * * * *